(12) United States Patent
Bonelli et al.

(10) Patent No.: US 11,604,192 B2
(45) Date of Patent: Mar. 14, 2023

(54) IMMUNOASSAY FOR DETECTING ZIKA VIRUS INFECTION

(71) Applicant: DiaSorin S.p.A., Saluggia (IT)

(72) Inventors: Fabrizio Bonelli, Casale Monferrato (IT); Tina Bunnell, Oakdale, MN (US); James Wassenberg, Falcon Heights, MN (US)

(73) Assignee: DiaSorin Italia S.p.A., Saluggia (IT)

( * ) Notice: Subject to any disclaimer, the term of this patent is extended or adjusted under 35 U.S.C. 154(b) by 438 days.

(21) Appl. No.: 16/494,913

(22) PCT Filed: Mar. 20, 2018

(86) PCT No.: PCT/EP2018/056990
§ 371 (c)(1),
(2) Date: Sep. 17, 2019

(87) PCT Pub. No.: WO2018/172337
PCT Pub. Date: Sep. 27, 2018

(65) Prior Publication Data
US 2020/0025760 A1   Jan. 23, 2020

Related U.S. Application Data

(60) Provisional application No. 62/473,548, filed on Mar. 20, 2017.

(51) Int. Cl.
*G01N 33/543* (2006.01)
*G01N 33/569* (2006.01)

(52) U.S. Cl.
CPC . *G01N 33/56983* (2013.01); *G01N 2333/185* (2013.01); *G01N 2800/26* (2013.01)

(58) Field of Classification Search
None
See application file for complete search history.

(56) References Cited

U.S. PATENT DOCUMENTS

| | | | | |
|---|---|---|---|---|
| 2009/0246800 A1* | 10/2009 | Mattingly | ........ | G01N 33/54326 435/7.1 |
| 2018/0136225 A1* | 5/2018 | Wong | .................. | G01N 33/6854 |
| 2018/0238881 A1* | 8/2018 | Lu | ................... | G01N 33/54386 |
| 2020/0158728 A1* | 5/2020 | Robinson | .......... | G01N 33/6854 |

FOREIGN PATENT DOCUMENTS

CN        105954512        9/2016

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Dupont et al., Q Fever Serology: Cutoff Determination for Microimmunofluorescence, Clinical and Diagnostic Laboratory Immunology, Mar. 1994, pp. 189-196. (Year: 1994).*
Sasso et al., Automated microfluidic processing platform for multiplexed magnetic bead immunoassays, Microfluid Nanofluidics, Oct. 2012; 13(4), pp. 1-20. (Year: 2012).*
CDPH Zika Virus Testing FAQs for Healthcare Providers, Jul. 5, 2016, pp. 1-7. (Year: 2016).*
Rodriguez et al., Microsphere-Based Immunoassy for the detection of Azaspiracids, Anal Biochem, Feb. 15, 2014; 447: pp. 1-14. (Year: 2014).*
Anonymous (2016) "*Anti-Zika Virus ELISA (IgM) Test Instruction,*" Euroimmun pp. 1-8 (Retrieved from the Internet: URL:http://www.fishersci.com/content/dam/fishersci/enUS/documents/programs/healthcare/technicaT-documents/package-inserts/zika-test-package-insert.pdf [retrieved on May 31, 2016].
Huzly, D. et al. (2016) "*High Specificity of a Novel Zika Virus ELISA in European Patients After Exposure to Different Flaviviruses,*" Euro Surveillance 21(16):pii=30203 (4 pages).
International Search Report PCT/EP2018/056990 (WO 2018/172337) (dated 2018) (6 pages).
Shan, C. et al. (2017) "*A Rapid Zika Diagnostic Assay to Measure Neutralizing Antibodies in Patients,*" EBiomedicine 17(1):157-162.
Sloan, A. et al. (2018) "*Evaluation of the DiaSorin Liaison® XL Zika Capture IgM CMIA for Zika Virus Serological Testing,*" Diagnostic Microbiology and Infectious Disease 90(4):264-266.
Steinhagen, K. et al. (2016) "*Serodiagnosis of Zika Virus (ZIKV) Infections by a Novel NS1-Based ELISA Devoid Of Cross-Reactivity with Dengue Virus Antibodies: A Multicohort Study of Assay Performance, 2015 to 2016,*" Euro Surveillance 21(50):pii=30426 (16 pages).
Theel, E.S. et al. (2018) "*Diagnostic Testing for Zika Virus: A Post-Outbreak Update,*" J. Clin. Microbiol. 56(4):pii=e01972-17; doi:10.1128/JCM.01972-17 (28 pages).
Written Opinion of the International Searching Authority PCT/EP2018/056990 (WO 2018/172337) (dated 2018) (6 pages).

(Continued)

*Primary Examiner* — Gary Counts
(74) *Attorney, Agent, or Firm* — Jeffrey I. Auerbach; Auerbach, LLC

(57) ABSTRACT

A biological sample, for example blood, serum, or plasma, is evaluated for the presence of anti-Zika virus (ZIKV) IgM- and IgG antibodies specific for ZIKV nonstructural protein 1 (NS1) by measuring the signal intensities of such antibodies in an immunoassay of the sample. Subjects are scored as being positive or negative for ZIKV infection based on the combined results of such determinations.

14 Claims, No Drawings

(56) References Cited

OTHER PUBLICATIONS

Zhang, B. et al. (2017) "*Diagnosis of Zika Virus Infection on a Nanotechnology Platform,*" Nature Med. 23(5):548-550.

Song, H., et al., (2016) "*Zika Virus NS1 Structure Reveals Diversity of Electrostatic Surfaces Among Flaviviruses*", Nat. Structural & Mol. Biology 23:456-459.

Stettler, K., et al. (2016), "*Specificity, Cross-Reactivity and Function of Antibodies Elicited by Zika Virus Infection*", Science 353(6301):823-826.

Baer, A. et al. (2014) "*Viral Concentration Determination Through Plaque Assays: Using Traditional And Novel Overlay Systems,*" J. Visualized Exper. (93):e52065:1-10.

Ribeiro, M. et al. (2020) "*Plaque Reduction Neutralization Test (PRNT) in the Congenital Zika Syndrome: Positivity and Associations with Laboratory, Clinical, and Imaging Characteristics,*" Viruses 12(11):1244:1-13.

\* cited by examiner

IMMUNOASSAY FOR DETECTING ZIKA VIRUS INFECTION

CROSS-REFERENCE TO RELATED APPLICATIONS

This application is a § 371 National Stage Application of PCT/EP2018/056990 (filed on Mar. 20, 2018), which application claims benefit of U.S. Patent Application No. 62/473,548 (filed on Mar. 20, 2017). Each of these applications is hereby incorporated by reference in its entirety.

FIELD OF THE INVENTION

The present invention relates to a method for detecting Zika virus infection in a biological sample from a subject. The biological sample is preferably blood, serum, plasma, cerebrospinal fluid, saliva or urine.

BACKGROUND OF THE INVENTION

Zika virus (ZIKV) is a mosquito-borne flavivirus in the family Flaviviridae and is closely related to dengue, yellow fever, Japanese encephalitis, and West Nile viruses. It is primarily transmitted by *Aedes* mosquitoes but can also be sexually transmitted. While most people infected with Zika virus do not have symptoms, Zika virus infection during pregnancy has been linked to microcephaly and other neurological complications. Detection of IgM antibodies to Zika virus provides an important tool for diagnosis and follow up care for an acute or recent Zika virus infection. Virus-specific IgM antibodies are typically present after the first week of illness and may be detectable for up to 12 weeks.

Similar to other flaviviruses, Zika virus is a membrane-enveloped virus with an icosahedral capsid structure and a single positive-sense RNA genome. The RNA genome encodes three structural proteins and seven nonstructural (NS) proteins. One of the structural proteins is the envelope (E) protein that encapsulates the virus and is the main target of neutralizing antibodies. The nonstructural protein 1 (NS1) is secreted by infected cells as a hexameric lipoprotein particle and is involved in immune evasion and pathogenesis. NS1 is the only nonstructural protein secreted from infected cells and is another target of the immune response.

There exist several significant challenges in developing a diagnostic test for Zika virus IgM antibodies. The most common problem of Zika virus serological tests is the extensive cross-reactivity of antibodies elicited by this virus with other flaviviruses, such as dengue and West Nile virus, which share a high degree of sequence homology with Zika virus. Commercially available assays for the serological diagnosis of Zika virus infections typically rely on the use of ZIKV envelope glycoproteins, such as the E glycoprotein, or NS1 protein as antigen reagents.

The E glycoprotein is the most immunogenic viral antigen and it has been widely used in diagnostic tests for the detection of flavivirus-specific human IgM antibodies in order to maximize diagnostic sensitivity.

The Centers for Disease Control and Prevention (CDC) have developed an antibody capture enzyme-linked immunosorbent assay (Zika MAC-ELISA) for the qualitative detection of Zika virus IgM antibodies in serum or cerebrospinal fluid. The Zika MAC-ELISA involves the use of anti-human IgM antibodies to bind the corresponding IgM antibodies of the sample. The detection of Zika-specific IgM is achieved by means of Zika E antigen along with an enzyme-conjugated anti-viral antibody.

Also the InBios "ZIKV Detect™ IgM Capture ELISA" makes use of the Zika virus envelope glycoproteins in a reverse capture format to detect circulating IgM antibodies against these viral proteins.

However, human antibodies against the E glycoprotein are cross reactive among flavivirus species. Assays which employ such protein as antigen component reportedly exhibit a high level of cross reactivity to other flaviviruses and usually require several additional calculations and laborious and expensive confirmatory retesting for the final reporting.

To minimize the likelihood of false-positive results, presumed positive or equivocal assay results obtained with the CDC "Zika MAC-ELISA" assay require confirmation by plaque-reduction neutralization testing (PRNT). PRNT is a labor-intensive procedure and not readily amenable to high throughput, making it difficult to use for large-scale surveillance and vaccine trials.

In the Inbios assay, the discrimination between positive and negative specimens involves a complex confirmative test, which includes comparing the Zika virus IgM values with sample reactivity measured versus non-specific antigens such as a Flavivirus common antigen and a mammalian cell common antigen.

Antibodies directed against the viral NS1 protein show a reduced degree of cross-reactivity between different flaviviruses. Indeed, the comparison of NS1 protein from dengue, West Nile and Zika virus revealed diverse electrostatic characteristics in the loop surface interface, which may result in altered binding properties (Song et al. Nat Struct Mol Biol. 2016; 23:456-458). Additionally, antibodies to NS1 from Zika virus infected patients were shown to be specific for Zika virus while antibodies against the E protein are highly cross-reactive to Dengue virus NS1 (Stettler et al. Science. 2016 Aug. 19; 353(6301):823-6).

In the "Anti-Zika virus ELISA" provided by Euroimmun a recombinant Zika NS1 protein is used as antigen component in an indirect IgM capture ELISA.

However, immunoassay methods which make use of the NS1 protein as antigen reagent have demonstrated poor diagnostic sensitivity, due to a significant prevalence of false-negative results, leading to risks and uncertainties.

Besides the risk of either cross-reactivity or low sensitivity, serological tests for Zika virus face the challenge of detecting IgM antibodies in patients with previous flavivirus exposure, as these subjects often exhibit a weak IgM response to Zika virus infection even in the acute phase. Seroconversion rates of IgM and IgG are different between primary and secondary dengue virus infections. During a secondary infection, patients often exhibit a weaker and shorter IgM response along with a stronger IgG response than during a primary dengue infection. A similar response occurs in patients with a Zika virus infection who have had previous flavivirus exposure. Patients without prior flavivirus exposure are expected to produce a typical seroconversion profile following Zika virus infection, while patients who have had previous flavivirus exposure exhibit a shorter and weaker IgM response. Correspondingly, these patients also exhibit a much stronger IgG response. This is particularly relevant as Zika virus is widely circulating in areas endemic for other flaviviruses thereby posing a significant challenge for serodiagnostics.

Thus, there exists a need in the art to develop a method for the diagnosis of Zika virus infection which overcomes the drawbacks and limitations of the prior art.

In particular, there is a need for an immunological method which would enable the specific and reliable detection of Zika virus infection without exhibiting substantial cross-reactivity with antibodies triggered by different flavivirus infections.

There is also a need for an immunological method with improved diagnostic sensitivity of Zika virus infections in subjects who are likely to have a high background exposure to other related flaviviruses.

These and other needs are met by an in vitro method for the detection of Zika virus (ZIKV) infection as defined in appended claim 1.

The detection method of the invention makes use of a diagnostic procedure that takes advantage of the strength of the IgM response to the more specific NS1 protein in primary infections and the strength of the IgG response in secondary infections. Further features and advantages of the method of the invention are defined in the dependent claims.

DETAILED DESCRIPTION

The present invention relates to an in vitro method for the detection of Zika virus (ZIKV) infection in a biological sample from a subject, comprising the steps of:
  a) testing the sample for IgM antibodies specific to ZIKV NS1 protein or an epitope or immunogenic fragment thereof and determining the ZIKV IgM signal intensity;
  b) testing the sample for IgG antibodies to ZIKV NS1 protein or an epitope or immunogenic fragment thereof and determining the ZIKV IgG signal intensity;
  c) establishing a first ZIKV IgM signal intensity threshold and a second ZIKV IgM signal intensity threshold, wherein the second ZIKV IgM signal intensity threshold is higher than the first ZIKV IgM signal intensity threshold;
  d) establishing at least a third ZIKV IgG signal intensity threshold;
  e) detecting the presence or absence of ZIKV infection in the sample according to the following criteria:
    i) a ZIKV IgM signal intensity lower than the first ZIKV IgM signal intensity threshold is indicative of the absence of ZIKA infection;
    ii) a ZIKV IgM signal intensity higher than the second ZIKV IgM signal intensity threshold is indicative of the presence of ZIKA infection;
    iii) when the ZIKV IgM signal intensity is higher than the first ZIKV IgM signal intensity threshold and lower than or equal to the second ZIKV IgM signal intensity threshold:
      iiia) a ZIKV IgG signal intensity lower than the at least third ZIKV IgG signal intensity threshold is indicative of the absence of a ZIKV infection; and
      iiib) a ZIKV IgG signal intensity higher than the at least third ZIKV IgG signal intensity threshold is indicative of the presence of a ZIKV infection.

As illustrated below, the method of the invention was designed to improve diagnostic accuracy of a recent Zika virus infection by combining the use of the more specific NS1 protein with a unique assay procedure.

The inventors found that the use of the NS1 protein as the detection reagent confers Zika virus specificity against other flaviviruses, while the assay procedure maximizes diagnostic sensitivity in subjects with previous flavivirus exposure and improves specificity in non-infected individuals.

In one embodiment, the method of the present invention relies on two distinct (separate) antibody capture immunoassays which are preferably carried out on the same biological fluid sample and aim at detecting Zika virus IgM and IgG antibodies, respectively, directed against the NS1 viral protein. The assessment of the presence or absence of Zika virus infection is determined according to the combined results provided by the Zika IgM and Zika IgG immunoassays.

In a preferred embodiment of the method of the invention, IgM-class and/or IgG-class antibodies present in the biological fluid sample are captured on solid surfaces coated with IgM binding molecules and IgG binding molecules, respectively.

Antibodies against viral NS1 proteins are known to be present at low levels in serum after flavivirus infections, probably due to a relative abundance of antibodies to the premembrane (prM) and envelope (E) structural proteins of flaviviruses, thus resulting in lower sensitivity of NS1 isotype immunoassays. For instance, in acute dengue serum specimens, anti-NS1 IgM antibodies are in the minority population compared to anti-virus like particles (VLP) IgM antibodies, presumably 3- to 12-fold lower than anti-VLP antibodies levels in the human serum, depending on the timing of serum collection. Consequently, the anti-NS1 IgM antibodies do not have a sufficiently high titer to compete with anti-VLP IgM antibodies in IgM-capture assays. In prior art anti-Dengue IgM assays, such a problem was addressed by including the depletion of anti-prM/E antibodies and a significant increase of the assay positive/negative (P/N) ratio value was achieved.

The present inventors found that a IgM- or IgG capture surface on which antibody binding molecules are immobilized in an amount corresponding essentially to the amount of total IgM and IgG antibodies in the tested sample enable the detection of specific anti-NS1 IgM- or IgG antibodies also when present in very small amounts, thereby significantly improving the sensitivity of the diagnostic assay. As an additional advantage, the use of such a solid surface for capturing total IgM antibodies present in the tested sample avoids the need for any enrichment step of the fraction of specific anti-NS1 IgM antibodies, for example by depleting anti-VLP IgM antibodies as in the prior art assays. At the same time, the use of the IgG capture surface in the method of the invention allows to capture all the tested IgG, thus being able to detect peak levels of Zika virus NS1-specific IgG antibodies, as it would only occur during a more recent infection.

Therefore, in a preferred embodiment of the method of the invention, Zika virus NS1-specific IgM and IgG antibodies are captured on a solid surface by contacting a biological sample with IgM binding molecules and/or IgG binding molecules immobilized on the solid surface in an amount which corresponds substantially to the amount of total IgM and IgG antibodies contained in the tested biological sample.

In the context of the present disclosure, the expression "biological sample" is intended to mean a pre-determined volume of the biological fluid used in the method of the invention.

In a more preferred embodiment, the biological fluid sample undergoes a dilution step before incubation with the IgG antibody capture surface. Preferably, the sample dilution factor is comprised between 10-fold and 500-fold, preferably between 50-fold and 200-fold, more preferably it is of about 90-fold. The use of such a sample pre-dilution step ensures the detection of peak levels of IgG antibodies to Zika virus.

In the method of the invention, a solid surface is used for capturing IgM- and/or IgG antibodies. Non limiting examples of suitable solid supports are the wells of a microtitre plate, the surface of a microparticle such as a latex, polystyrene, silica, chelating sepharose or magnetic beads, membranes, strips or chips. Preferably, the solid support is a bead, more preferably a paramagnetic microparticle (PMP). The IgM- and/or IgG-binding molecule may be covalently bound to the solid surface, or non-covalently attached through nonspecific bonding.

According to an embodiment of the invention, the antibody binding protein immobilized on the solid surface is an anti-IgG antibody, an anti-IgM antibody, an immunoglobulin-binding peptide or a peptidomimetics. Especially preferred are anti-IgM antibodies and anti-IgG antibodies, even more preferably monoclonal anti-IgM and anti-IgG antibodies.

In the context of the present invention, the biological fluid sample is preferably selected from the group consisting of whole blood, serum, plasma, cerebrospinal fluid, urine or saliva. The biological fluid sample may optionally include further components, such as for example: diluents, preservatives, stabilizing agents and/or buffers. If needed, dilutions of the biological fluid sample are prepared using any suitable diluent buffer known in the art.

According to the method of the present invention, the detection of Zika virus NS1-specific IgM and/or IgG antibodies captured on the solid surface is performed by employing the NS1 antigen, epitope or a fragment thereof.

In a preferred embodiment of the invention, the NS1 protein used as the detection reagent is the whole recombinant protein; alternatively, it is an epitope or an immunogenic fragment of the Zika virus NS1 protein.

In one embodiment of the invention, the NS1 antigen is labeled with means capable of providing directly or indirectly a detectable signal. Suitable labels for use in the present invention include for example fluorescent compounds, chemiluminescent compounds, radioactive compounds, enzymes and enzyme substrates, molecules suitable for colorimetric detection, binding proteins, epitopes, enzymes or substrates. In practice, any signal molecule or label known in the art may be used in the method of the present invention. In another embodiment, the means capable of indirectly providing a detectable signal comprise an antibody that binds to the antigen, for example an anti-NS1 antibody. Such antibody may be provided with direct or indirect label means as described above for the antigen.

In still yet another embodiment, the Zika IgM and Zika IgG immunoassays comprise i) contacting the biological sample with IgM binding molecules coated on a solid surface in an amount corresponding substantially to the amount of IgM antibodies in said sample, thereby capturing the IgM antibodies in the sample, ii) contacting the biological sample with IgG binding molecules coated on a solid surface in an amount corresponding substantially to the amount of IgG antibodies in said sample, thereby capturing the IgG antibodies in the sample, and iii) detecting captured ZIKV IgM antibodies and ZIKV IgG antibodies specific to ZIKV NS1 protein employing a labeled ZIKV NS1 antigen, epitope or fragment thereof.

The diagnostic assessment of the patient's sample relies upon the intensity of the respective signals obtained from the ZIKV IgM- and ZIKV IgG-assays. In a specific embodiment, an automatic analyzer is used which extrapolates the signal intensities on calibration standard curves to obtain a IgM index and a IgG index. Then, the analyzer combines the two index values to produce a single result. In the method of the invention, the calibration standard curve may be generated, for example, by using human serum or defribinated plasma samples containing known amounts of Zika virus IgM or Zika virus IgG.

The Zika IgM test consists of both a high and a low cut-off value (threshold) for the IgM index. Specimens below the low cut-off value are considered Zika IgM negative and specimens above the high cut-off value are considered Zika IgM positive. Specimens between the two cut-off values are resolved by the result of the Zika IgG test. Stated another way, diagnostic sensitivity is achieved through the use of a low cut-off value for the Zika IgM test only in the presence of detectable Zika IgG antibodies. In the absence of detectable Zika IgG antibodies, a higher cut-off value for the Zika IgM test is used thereby maximizing specificity in non-infected individuals. In this way, the Zika IgG test helps to differentiate a true negative specimen from a specimen exhibiting a weak IgM response due to a secondary flavivirus infection. As such, the diagnostic assessment procedure maximizes diagnostic sensitivity and specificity. This approach is particularly effective in endemic regions because of the use of an IgG assay that only detects peak levels of IgG during a recent infection.

Subjects without prior exposure to flaviviruses exhibit a strong IgM response following infection with Zika virus and are detected using the higher cut-off value for the Zika IgM test regardless of the Zika IgG result. Subjects who have had previous exposure to another flavivirus may exhibit a weak IgM response but a strong IgG response and are therefore detected through the use of the low cut-off value.

According to a specific embodiment of the invention, the following diagnostic assessment procedure is used:
(i) IgM and IgG tests are run at the same time on a sample;
(ii) samples with an IgM result below a first lower threshold are scored as "negative";
(iii) samples with an IgM result above a second higher threshold value are scored as "positive";
(iv) for samples with an IgM result between the lower threshold and higher threshold, the IgG result is examined and those samples with an IgG result above a third IgG threshold are scored as "positive", while those with an IgG result below the third IgG threshold are scored as "negative".

The following alternative embodiments of the diagnostic assessment procedure are also within the scope of the invention, in that they are the same in principal and effect to the procedure described above:

1. A multilevel IgG procedure, in which the procedure is similar to that described above, but more than one IgG cutoff is applied to the IgM result, leading to additional levels of diagnosis in addition to "negative" and "positive" (for example: negative, possible positive, presumptive positive, positive).
2. A reflex procedure, by which IgM is run, and IgM results that are in the equivocal region (or gray zone or reflex zone) are reflexed to an IgG assay for "confirmation" (High IgG=positive confirmation, Low IgG=negative or unconfirmed.)
3. A retest-reflex procedure, by which IgM is run, equivocals are retested on IgM, repeat equivocals are reflexed to IgG for "confirmation" or "differentiation".
4. A reverse order procedure, by which an IgG assay is run first, and the result of the IgG test determines to which of two possible IgM tests the sample is reflexed. A "negative", or low, IgG result reflexes to a sensitive (low cut-off) IgM test, and a "positive", or high, IgG result reflexes to an insensitive (high cut-off) IgM test.

5. A triple test, wherein IgA are tested in addition to IgM and IgG. The following examples are provided by way of illustration only and are not intended to limit the scope of the invention as defined in the appended claims.

Example 1 Antibody Immobilization on Solid Surface

MyOne paramagnetic-particles (PMPs) were coated at 0.5% with 30 μg/mg of α-human IgM antibody or α-human IgG antibody using a sodium sulfate coating buffer (1.6 mM Sodium Phosphate Monobasic, 18.3 mM Sodium Phosphate Dibasic and 9% Sodium Sulfate at pH 8.2). The PMPs were blocked with blocking buffer containing 0.5% BSA, and diluted to a final bead concentration of 3.75 mg/ml (0.375% particles) in storage buffer (1.8 mM Potassium Phosphate Monobasic, 10 mM Sodium Phosphate Dibasic, 114 mM Sodium Chloride, 2.7 mM Potassium Chloride, 0.05% Tween 20, 0.1% Bovine Serum Albumin, and 0.09% Sodium Azide at pH 7.4).

Example 2 Antigen Conjugate Preparation

A full length recombinant Zika virus NS1 antigen was buffer exchanged and conjugated at a target of 1× molar excess with cyclic N-(4-aminobutyl)-N-ethylisoluminol (ABEI) in PBS buffer pH 7.4. The conjugated antigen was then purified, diluted at a target concentration of 12.5 μg/ml in conjugate diluent (100 mM NaCl, 0.1% TWEEN 20®, 2 ml/L PROCLIN™, 1% BSA, 3% D-Mannitol, pH 7.4) and lyophilized. Before use in the method of the invention, the lyophilized conjugate was reconstituted in diH$_2$O and used on the ancillary bay of the analyzer.

Example 3 Detection of Zika Virus NS1-Specific IgM Antibodies

The assay aims at the detection of IgM antibodies against Zika virus NS1 present in serum samples, calibrators and controls. The calibrators and controls were composed of anti-Zika IgM positive serum diluted with defibrinated/delipidated serum. The assay was carried out on the DiaSorin LIAISON® XL analyzer. As an initial step, 20 μl of anti-IgM coated magnetic particles were dispensed into a reaction cuvette and incubated with 10 μl serum sample or control sample for 36 cycles (equivalent to a total of 12 minutes and 36 seconds). Unbound material was then removed by a washing step with Wash/System liquid. Subsequently, a total of 40 μl of cABEI-conjugate NS1 antigen and 250 μl assay buffer (100 mM NaCl, 0.1% TWEEN 20®, 3.0% Bovine Serum Albumin, and 0.2% PROCLIN 300™ at pH 7.4) were dispensed in the reaction cuvette, and a second incubation and washing step were carried out as above-described. After this second wash, Starter Reagents were added and a flash chemiluminescence reaction was induced. The light signal, and hence the amount of isoluminol-antigen conjugate, was measured by a photomultiplier as relative light units (RLU) in the analyzer reading chamber. Measured values were indicative of the presence of IgM antibodies to Zika virus NS1 in patient sera, calibrators, or controls.

The above-described assay steps were carried out on an automated instrument. The assay was calibrated using two point calibrators to obtain an instrument working curve based upon the assay master curve. Sample RLU values were then automatically converted to an Index value based on the instrument working curve.

Example 4 Detection of Zika Virus NS1-Specific IgG Antibodies

The assay aims at the detection of IgG antibodies against Zika virus NS1 present in serum samples, calibrators and controls. The calibrators and controls were composed of anti-Zika IgG positive serum diluted with defibrinated/delipidated serum. The assay was carried out on the DiaSorin LIAISON® XL analyzer. First, 15 μl of serum sample, calibrator or control were diluted in 130 μl specimen diluent (6.47 mM Sodium Phosphate dibasic, 1.18 mM Potassium Phosphate monobasic, 110 mM Sodium Chloride, 2.1 mM Potassium Chloride, 2.4 mM EDTA, 0.22% TWEEN 20®, 0.28%™ X705, 3.2% Bovine Serum Albumin and 0.2% PROCLIN 300™ at pH 6.5). Next, 15 μl of diluted sample were diluted again in 130 μl specimen diluent. Then, 200 μl of specimen diluent along with 20 μl of anti-IgG coated magnetic particles were dispensed into a reaction cuvette, followed by the addition of 8 μl of diluted sample, calibrator or control. The mixture was subjected to a first incubation for 36 cycles (equivalent to a total of 12 minutes and 36 seconds). After a first washing step with Wash/System liquid in order to remove unbound material, 40 μl of cABEI-conjugate NS1 antigen and 250 μl assay buffer (100 mM NaCl, 0.1% TWEEN 20®, 3.0% Bovine Serum Albumin, and 0.2% PROCLIN 300™ at pH 7.4) were dispensed in the reaction cuvette, and the incubation and wash step were carried out again as above-described. After the second wash, Starter Reagents were added and a flash chemiluminescence reaction was induced. The light signal, and hence the amount of isoluminol-antigen conjugate, was measured by a photomultiplier as relative light units (RLU) in the analyzer reading chamber. Measured values were indicative of the presence of IgG antibodies to Zika virus NS1 in patient sera, calibrators, or controls.

The above-described assay steps were carried out on an automated instrument (DiaSorin LIAISON® XL analyzer). Each reagent pack was calibrated using two point calibrators to obtain an instrument working curve based upon the assay master curve. Sample RLU values were then automatically converted to an Index value based on the instrument working curve for each reagent pack.

The DiaSorin LIAISON® XL analyzer automatically calculates an Index value for both the ZIKV-M and ZIKV-C reagent packs based on each individual calibration. The analyzer then automatically combines the two Index values to produce a single result. Table 1 below shows the results obtained from examples 3 and 4, expressed in terms of M Index and C Index values, and corresponding diagnostic assessment.

TABLE 1

| ZIKV-M (IgM) Index | ZIKV-C (IgG) Index | Result |
|---|---|---|
| <1.0 | Any Value | Negative |
| ≥1.0 to <2.2 | <4.0 | |
| | ≥4.0 | Positive |
| ≥2.2 | Any Value | |

Example 5 Diagnostic Sensitivity of the Zika Virus Assay

In order to assess the sensitivity of the Zika Capture IgM assay of the invention, positive agreement was evaluated using serially collected serum samples from 58 symptomatic subjects (including 15 pregnant women) from the Dominican Republic found to be initially PCR positive for Zika virus. Multiple serial collections were obtained for 39 of the subjects and a single collection between 8 and 14 days post-symptom onset was obtained for 19 subjects.

As shown in Table 2 below, all 58 positive subjects were reported as Zika IgM positive in the Zika Capture IgM assay. For serial collections, a positive Zika IgM result was obtained by the first draw following 8 days post onset of symptoms.

TABLE 2

Positive Agreement*

| Population | LIAISON ® XL Zika Capture IgM | | | |
|---|---|---|---|---|
| | Positive | Negative | Total | Positive Agreement |
| Non-Pregnant | 43 | 0 | 43 | 100% |
| Pregnant | 15 | 0 | 15 | 100% |
| TOTAL: | 58 | 0 | 58 | 100% |

*For serial collections, only the first positive result was included. Positive Percent Agreement: 100% (58/58, 95% CI: 93.8-100%)

The time course of Zika IgM detection in the Zika Capture IgM assay was assessed using all 188 specimens collected from the 58 subjects (Table 3).

TABLE 3

Time Course of IgM Detection in Positive Subjects

| Days Post Symptom | LIAISON ® XL Zika Capture IgM | | | |
|---|---|---|---|---|
| Onset | Positive | Negative | Total | % Zika IgM Detection |
| ≤3 | 0 | 10 | 10 | 0% |
| 4-7 | 5 | 24 | 29 | 17% |
| 8-14 | 48 | 1* | 49 | 98% |
| 15-21 | 31 | 0 | 31 | 100% |
| 22-28 | 21 | 1 | 22 | 95% |

TABLE 3-continued

Time Course of IgM Detection in Positive Subjects

| Days Post Symptom | LIAISON ® XL Zika Capture IgM | | | |
|---|---|---|---|---|
| Onset | Positive | Negative | Total | % Zika IgM Detection |
| 29-42 | 23 | 2 | 25 | 92% |
| 43-84 | 16 | 6 | 22 | 73% |

*Specimen RT-PCR positive at 8 days post symptom onset

Example 5 Diagnostic Specificity of the Zika Virus Assay

The diagnostic specificity of the Zika Capture IgM assay of the invention was assessed by evaluating negative agreement using serum samples from 218 apparently healthy donors and 32 pregnant donors collected in the United States and presumed negative for Zika virus infection. The results of the evaluation are reported in Table 4 below. Negative percent agreement was found to be 99.6%.

TABLE 4

Negative Agreement

| Population | LIAISON ® XL Zika Capture IgM | | | |
|---|---|---|---|---|
| | Positive | Negative | Total | Negative Agreement |
| Pregnant Donors | 0 | 32 | 32 | 100.0% |
| Normal Donors | 1 | 217 | 218 | 99.5% |
| TOTAL: | 1 | 249 | 250 | 99.6% |

Negative Percent Agreement: 99.6% (249/250, 95% CI: 97.4-99.7%)

Example 6 Cross-Reactivity of the Zika Virus Assay

In order to assess possible cross-reactivity of the Zika Capture IgM assay of the invention, specimens were analyzed which are seropositive for other closely related viruses or microorganisms. The results of the cross-reactivity analysis are summarized in Table 5 below.

TABLE 5

| | Organism/Condition | N | LIAISON ® XL Zika Capture IgM | | % Cross Reactivity |
|---|---|---|---|---|---|
| | | | Positive | Negative | |
| Flaviviruses | Anti-Dengue virus (IgM) | 10 | 0 | 10 | 0% |
| | Anti-West Nile Virus (IgM) | 14 | 0 | 14 | 0% |
| | Yellow fever virus post-immunization | 10 | 0 | 10 | 0% |
| Other Viruses/diseases | Anti-Chikungunya virus (IgM) | 5 | 0 | 5 | 0% |
| | Anti-Cytomegalovirus (IgM) | 3 | 0 | 3 | 0% |
| | Anti-Epstein Barr Virus (IgM) | 3 | 0 | 3 | 0% |
| | Anti-Parvovirus B19 (IgM) | 5 | 0 | 5 | 0% |
| | Anti-Varicella zoster virus (IgM) | 5 | 0 | 5 | 0% |
| | Anti-nuclear Antibodies (ANA) | 3 | 0 | 3 | 0% |
| | Anti-Malaria/anti-*plasmodium falciparum* | 3 | 0 | 3 | 0% |
| | Anti-Hepatitis (C) virus (optional) | 5 | 0 | 5 | 0% |
| | Enterovirus (optional) | 3 | 0 | 3 | 0% |

The invention claimed is:

1. An in vitro method for the detection of Zika virus (ZIKV) infection in a human subject, comprising the steps of:
   a) testing a first portion of a sample of said subject's blood, serum or plasma for IgM antibodies specific to ZIKV NS1 protein or an epitope or immunogenic fragment thereof and determining a ZIKV IgM signal intensity, wherein said testing comprises:
      (1) contacting said first portion of said sample with beads that are coated with IgM binding molecules, wherein said contacting is under conditions sufficient to permit the capture of said ZIKV NS1-specific IgM antibodies, if present in said sample, to the surface of said beads, and wherein the amount of IgM binding molecules coated on the surface of said beads substantially corresponds to the amount of IgM antibodies present in said sample; and
      (2) conducting an immunoassay using said ZIKV NS1 protein or epitope or immunogenic fragment thereof as a detection reagent, wherein said immunoassay is conducted under conditions sufficient to permit the detection of a ZIKV IgM signal intensity from captured ZIKV NS1-specific IgM antibodies if present in said sample;
   b) testing a second portion of said sample of said subject's blood, serum or plasma for IgG antibodies to ZIKV NS1 protein or an epitope or immunogenic fragment thereof and determining a ZIKV IgG signal intensity, wherein said testing comprises:
      (1) contacting said second portion of said sample with beads that are coated with IgG binding molecules, wherein said contacting is under conditions sufficient to permit the capture of said ZIKV NS1-specific IgG antibodies, if present in said sample, to the surface of said beads, and wherein the amount of IgG binding molecules coated on the surface of said beads substantially corresponds to the amount of IgG antibodies present in said sample; and
      (2) conducting an immunoassay using said ZIKV NS1 protein or epitope or immunogenic fragment thereof as a detection reagent, wherein said immunoassay is conducted under conditions sufficient to permit the detection of a ZIKV IgG signal intensity from captured ZIKV NS1-specific IgG antibodies if present in said sample;
   c) establishing a first ZIKV IgM signal intensity threshold and a second ZIKV IgM signal intensity threshold, wherein the second ZIKV IgM signal intensity threshold is higher than the first ZIKV IgM signal intensity threshold; and
   d) establishing at least a third ZIKV IgG signal intensity threshold;
   wherein ZIKV infection is determined based on the combined results of said detected ZIKV IgM signal intensity and said detected ZIKV IgG signal intensity, wherein:
      i) a ZIKV IgM signal intensity from said first portion of said sample of said subject's blood, serum or plasma that is lower than the first ZIKV IgM signal intensity threshold is indicative of the absence of ZIKV infection in said subject;
      ii) a ZIKV IgM signal intensity from said first portion of said sample of said subject's blood, serum or plasma that is higher than the second ZIKV IgM signal intensity threshold is indicative of the presence of ZIKV infection in said subject;
      iii) when said first portion of said sample of said subject's blood, serum or plasmas exhibits a ZIKV IgM signal intensity that is higher than the first ZIKV IgM signal intensity threshold and lower than or equal to the second ZIKV IgM signal intensity threshold:
         iiia) a ZIKV IgG signal intensity from said second portion of said sample of said subject's blood, serum or plasma that is lower than the at least third ZIKV IgG signal intensity threshold is indicative of the absence of a ZIKV infection in said subject; and
         iiib) a ZIKV IgG signal intensity from said second portion of said sample of said subject's blood, serum or plasma that is higher than the at least third ZIKV IgG signal intensity threshold is indicative of the presence of a ZIKV infection in said subject.

2. The method according to claim 1, wherein step a) and/or step b) are repeated.

3. The method according to claim 1, wherein step a) is carried out before step b).

4. The method according to claim 1, wherein step a) is carried out after step b).

5. The method according to claim 1, which also includes testing the sample for IgA antibodies specific to ZIKV NS1 protein or an epitope or immunogenic fragment thereof.

6. The method according to claim 1, wherein the IgM binding molecules are anti-human IgM antibodies.

7. The method according to claim 1, wherein the IgG binding molecules are anti-human IgG antibodies.

8. The method according to claim 1, wherein said beads that are coated with said IgM binding molecules are magnetic beads.

9. The method according to claim 1, wherein one or both of said steps a) and b) comprises a chemiluminescent immunoassay.

10. The method according to claim 9, which employs an isoluminol derivative as a chemiluminescent label.

11. The method according to claim 1, wherein in step b) said second portion of said sample of said subject's blood, serum or plasma, before contacting the IgG binding molecules coated on said beads, is diluted by a dilution factor comprised between 10-fold and 500-fold.

12. The method according to claim 1, wherein ZIKV IgM and/or ZIKV IgG signal intensities are determined by reference to a calibration curve.

13. The method according to claim 1, wherein the infection is a secondary flavivirus infection.

14. The method according to claim 1, wherein said beads that are coated with said IgG binding molecules are magnetic beads.

* * * * *